(12) United States Patent
Bostrom et al.

(10) Patent No.: US 7,658,092 B2
(45) Date of Patent: Feb. 9, 2010

(54) HEAT SWITCH FOR CHROMATOGRAPHIC SYSTEM AND METHOD OF OPERATION

(75) Inventors: Neil William Bostrom, Cambridge, MA (US); Shigeo Daito, Lexington, MA (US); Jagdish Shah, Southington, CT (US); Robert L. Kleinberg, Cambridge, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 45 days.

(21) Appl. No.: 11/615,426

(22) Filed: Dec. 22, 2006

(65) Prior Publication Data
US 2008/0148814 A1 Jun. 26, 2008

(51) Int. Cl.
*G01N 30/02* (2006.01)
(52) U.S. Cl. ............... 73/23.35; 73/23.25; 73/23.41
(58) Field of Classification Search ........... 73/23.25, 73/23.35, 23.41
See application file for complete search history.

(56) References Cited

U.S. PATENT DOCUMENTS

| | | | | |
|---|---|---|---|---|
| 3,581,465 A | * | 6/1971 | Haruki et al. | 95/87 |
| 3,910,765 A | * | 10/1975 | Tinklepaugh et al. | 422/89 |
| 4,038,055 A | * | 7/1977 | Varano et al. | 96/102 |
| 4,739,654 A | | 4/1988 | Pilkington et al. | |
| 6,029,498 A | * | 2/2000 | Walters et al. | 73/23.39 |

FOREIGN PATENT DOCUMENTS

| | | | |
|---|---|---|---|
| FR | 2637685 A1 | * | 4/1990 |
| WO | 01/73424 A1 | | 10/2001 |

OTHER PUBLICATIONS

Colwell, J., "The Performance of a Mechanical Heat Switch at Low Temperatures", The Review of Scientific Instruments, vol. 40, No. 9, Sep. 1969.
Kakac et al., "Heat Conduction" Third Edition, pp. 54, 57-59, Taylor & Francis 1993.
Halliday et al., "Fundamentals of Physics", Fifth Edition, Chapter 19, Temperature, Heat, and the First Law of Thermodynamics, pp. 470-473, John Wiley & Sons, Inc. 1997.
Phillips et al., "Paraffin-Actuated Heat Switch for Mars Surface Applications", NASA Tech Brief vol. 26, No. 5 from JPL New Technology Report NPO-30351, May 1, 2002.
Chave et al., "Magnetostrictive Heat Switch for Cryogenic Use", NASA Tech Brief, Aug. 1999 from http://www.nasatech.com/Briefs/Aug99/NPO20274.html.

* cited by examiner

*Primary Examiner*—Daniel S Larkin
(74) *Attorney, Agent, or Firm*—James M. McAleenan; Jody Lynn DeStefanis; Helene Raybaud

(57) ABSTRACT

A heat switch for remote self-contained gas chromatography is disclosed. The device mechanically separates a hot or cold reservoir from the chromatography column when heating or cooling is not needed. The column needs a cooling system to obtain initial temperatures below ambient. At other times the column needs to be heated to relatively high temperatures, during which time the cooling system is preferably detached. The heat switch allows for rapid temperature changes while minimizing the peak cooling power requirement.

33 Claims, 4 Drawing Sheets

HEAT SWITCH FOR CHROMATOGRAPHIC SYSTEM AND METHOD OF OPERATION

BACKGROUND OF THE INVENTION

1. Field of Invention

The present invention relates to chromatographic systems and techniques of operation thereof and, more particularly, to gas chromatographic systems, subsystems, and techniques of operation involving heating and/or cooling chromatographic columns.

2. Background of the Invention

In existing chromatographic analysis, separation of components of an analyte typically occurs as the analyte moves through a column. The time for the components to traverse the column typically depends on the respective affinities of the components relative to the stationary phase. Because affinity is generally dependent on temperature, the temperature of the column is preferably controlled in a particular manner. Existing columns may further have temperature control which provides temperature regulation and/or ramping up of column temperature from a first temperature to a second higher temperature. Additionally, temperature control of a column may further include the need to ramp column temperature from a second higher temperature to a first lower temperature. For example, existing chromatography protocols typically start at low temperatures to provide sufficient resolution among the lighter components to be analyzed and then ramp up the temperature to elute the heavier components under analysis. For example, in existing chromatographic systems the initial column temperature may be slightly above ambient room temperature, for example, at about 40° C. During chromatographic separation, the temperature of the column may be increased at a predetermined rate and/or according to a predetermined schedule, resulting in a second higher column temperature. At the end of the analysis the column is preferably cooled as cooling the chromatographic column decreases the time between analyses, especially when the chromatographic systems are operated with one or more temperature increases.

The temperature of a column, and time spent at a predetermined temperature, is further related to the analyte under analysis. For example, chromatographic separation and analysis of a gas sample can generally be achieved in a shorter time and with lower maximum temperature to elute all components as compared to separation and analysis of heavy components of oils. Following the completion of the analysis, regardless of the analyte under analysis, a return of the column to a lower temperature is generally required. In light of the requirement, higher maximum temperatures which occur through temperature ramping for heavy components of an oil sample generally translate into longer cooling times before starting a subsequent analysis.

As understood by one skilled in the art, existing cooling methods include the use of forced convection utilizing ambient air. In some cases, however, forced convective cooling by ambient air is not possible, e.g., when the ambient air temperature is above the column temperature. Additionally techniques such as radiative or convective cooling are also employed in the prior art, but such systems are generally not practical in various environments. In a downhole environment, these existing techniques may not be appropriate or may be impossible when compared to conductive cooling techniques.

Further, attaching a cooling system directly to the column can create undesirable consequences because the attached cooling system increases the effective thermal mass of the column. When the columns are heated with a temperature ramp, the cooling system will also be heated. When the cooling system is needed, it will take longer to achieve the initial temperature due to the increased mass of the column. A larger thermal mass consequently requires a greater heating burden to achieve a particular rate of temperature increase. The increased power requirement may be a significant, especially in power limited environments such as a downhole environment. Further, the maximum allowable temperature of some cooling system components may below an operating temperature of one or more columns. For example, the maximum allowable temperature of Peltier coolers is typically about 225° C., thus the operating temperature of the column would be limited to below this temperature.

SUMMARY OF THE INVENTION

One or more aspects of the present invention are directed toward solving the thermal cooling concerns and limitations between bodies exhibited in the prior art. One embodiment of the present invention can be directed to analytical systems. The analytical system can comprise a chromatographic column having a first thermal body, a second thermal body having a surface, and an actuator configured to control thermal communication between at least a portion of the first thermal body and at least a portion of the second thermal body.

Further aspects of the invention can be directed to a method of characterizing an analyte in an analytical system having at least one chromatographic column. The method can comprise acts of introducing the analyte into the chromatographic column wherein the column has a first thermal body, raising the temperature of the chromatographic column from a first temperature to a second temperature and thermally coupling the first thermal body to a second thermal body.

Still further aspects of the invention can be directed to computer-readable media. The computer-readable medium can including computer-readable signals stored thereon defining instructions that, as a result of being executed by a computer, instruct the computer to perform a method of characterizing an analyte in an analytical system having at least one chromatographic column having a first thermal body, a second thermal body, and an actuator device configured to control thermal communication between the first thermal body and the second thermal body. The method may comprise of acts of raising the temperature of the chromatographic column from a first temperature to a second temperature and thermally coupling the first thermal body to the second thermal body.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. The present drawings illustrate several embodiments in keeping with the present invention. The selection of these embodiments, and the subsequent description of these embodiments, is solely for clarity and is not intended to limit the scope of that which is claimed. One skilled in the art will readily recognize that the present invention may be practiced in numerous alternative configurations in keeping with that which is recited herein.

DETAILED DESCRIPTION OF THE PREFERRED EMBODIMENTS

Figures 1A, 1B:
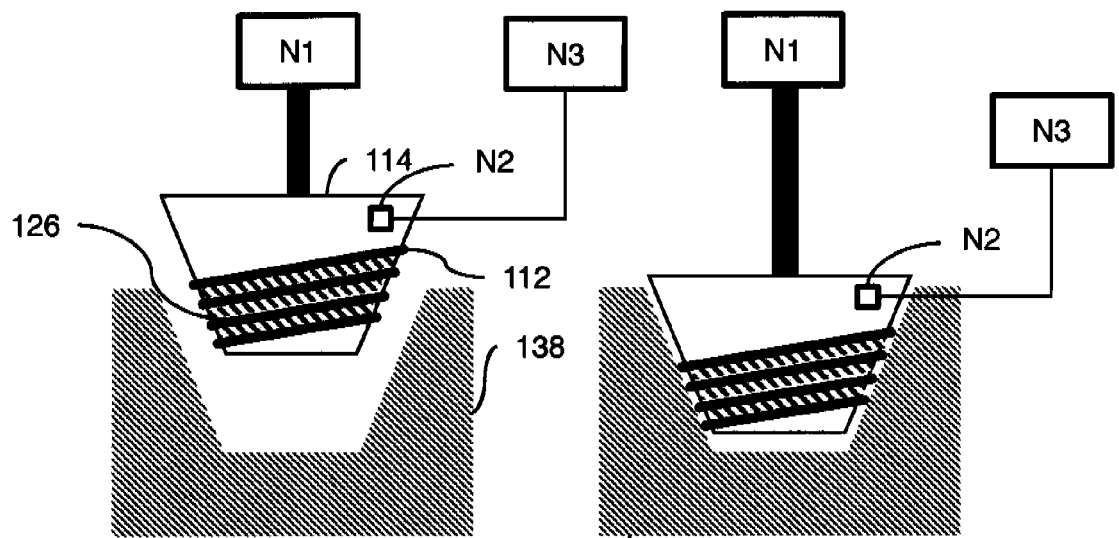
FIGS. 1A to 1D illustrate cooling and heating assemblies in accordance with one or more embodiments of the invention.

As used herein, the term "analyte" shall be defined as a sample under analysis. Additionally, the terms analyte and sample may be used interchangeably. Additionally the terms "chromatographic column" and "column" shall be used interchangeably without any limitation of scope. Furthermore, the term "analysis" shall be defined as a chromatographic analysis as understood by one skilled in the art. Additionally the term "thermal bodies" or "bodies" shall include a first thermal body having a first thermal mass and a second thermal body having a second thermal mass. In accordance with one embodiment of the present invention, a column may be in thermal communication with a first thermal body. Additionally the term "source" or "heat source" is herein defined as an environment or object that generates or supplies heat. Furthermore, as used herein the term "sink" or "heat sink" is herein defined as an environment or object that absorbs and dissipates heat from another object (a heat source).

In view of the foregoing limitations of conventional cooling techniques, the present invention facilitates column cooling by providing systems or subsystems and techniques that reduces the column temperature to the initial ramp temperature. Accordingly, some aspects of the invention are directed to cooling systems and techniques that can reduce the time between analyses. Further aspects of the present invention are directed to cooling systems and techniques that can maintain a predetermined column temperature.

As understood by one skilled in the art, temperature controlled columns may be disposed in a variety of environments. One such environment is a downhole environment, wherein the column is used to effectuate compositional analysis of an analyte such as a formation fluid. When located downhole, conventional chromatographic columns are typically operated at a temperature below the ambient temperature of the downhole environments. As understood by one skilled in the art, downhole conditions may reach about 200° C., thereby imposing great column cooling demands on a cooling mechanism used in maintaining a desired temperature of the column.

While some aspects of the present invention involve systems and techniques that facilitate operation of chromatographic systems disposed in a downhole or subsurface environment, the various aspects of the invention are not limited to such environments. One skilled in the art will readily recognize that one or more aspects of the present invention may be readily implemented in surface-based systems. For example, some particularly advantageous features of the invention can facilitate characterization of analytes by reducing the required column cooling period, and consequently, the overall analytical cycle time of laboratory-based chromatographic systems.

Some aspects of the present invention are further directed to systems and techniques that separate the cooling system, or a portion thereof, from the column when the cooling system is not required. Separation of the cooling system, or a portion thereof, in accordance with one embodiment of the present invention results in the reducing of the thermal mass during heating operations, thereby resulting in a decreased heating load. Such a reduction in the heat load is particularly beneficial when the column is operated in an environment where available power for heating is limited.

Further aspects of the invention may involve modifying the effective thermal mass of a heated and/or cooled body. For certain embodiments of the invention, changing the effective thermal mass of a body can be effected by establishing thermal communication between the body and one or more thermal sources or thermal sinks through, for example, conductive heat transfer. This approach can be particularly advantageous in certain operating conditions including, for example, in remote self-contained environments.

In accordance with the present invention, heat conduction between thermal bodies can be effected through a thermally conductivity material such as, but not limited to, copper (having a thermal conductivity of about 386 W/m·K). In one embodiment of the present invention, the thermal bodies may include a mandrel and an associated mating body. In alternative embodiments, the thermal bodies may include a first thermal body having a first thermal mass and a second thermal body having a second thermal mass. One skilled in the art will recognize that numerous alternative thermally conductive materials may be utilized in practicing the present invention, and may be selected based upon the required thermal characteristics or the intended operating environment. Additionally, as understood in the art, the thermally conductive material may further be modified, include but not limited to the application of surface treatments, coatings, etc., such that the required properties of the thermally conductive material are enhanced or preserved when in operation. Alternative embodiments of the present invention can comprise systems and techniques that provide a plurality of thermal sources and/or thermal sinks. As used herein, a thermal sink can be a body that accepts heat and a thermal source can be a body that has a thermal mass and is capable of transferring heat.

Some aspects of the invention can pertain to facilitating the contact between the bodies undergoing heat transfer to reduce, for example, the thermal resistance therebetween. Deformation at the contacting surfaces which can be created by an interference can change the effective thermal conduction transfer area between the two bodies and/or the thermal conduction properties of the thermally conductive material. For example, the present of roughness or dirt on or along the interface between bodies undergoing heat transfer may result in decreased thermal conductivity. Furthermore, the actual contact area between the bodies undergoing heat transfer may also depend on the applied load creating or affecting the contact.

Additionally degradation of the thermally conductive material, and the resulting degradation of the heat transfer of the bodies, may be further prevented in accordance with the present invention. For example, the presence of thermally insulating layers between the contacting surfaces can affect the heat transfer rate. Oxide films or any other poor conductor between the surfaces can also increase the contact resistance. Preferably, the materials comprising one or more of the transfer surfaces are selected to limit the presence, or creating of a layer that undesirably increases thermal contact resistance. Additionally, in accordance with the present invention an appropriate surface treatment may be applied to the thermally conductive material to facilitate heat transfer between the bodies. Thus, in accordance with one or more embodiments of the invention, at least a portion of the contacting surfaces comprises and/or is coated with an inert material. For example, the contacting surfaces can comprise a surface treatment including but not limited to an inert precious metal such as gold. The invention however is not limited as such and any material that does not readily form an oxide layer may be utilized as a portion of the contacting surface. In accordance with the present invention, suitable surface treatments may further include the application of appropriate chemical compositions or surface finishes, as understood by one skilled in the art, to effectuate thermal transfer between bodies.

In accordance with some embodiments of the invention, the material comprising at least one of the contacting surfaces of the thermally conductive material may comprise a metal or an alloy that can at least partially conform to the shape of the contacting body to at least partially increase the effective heat transfer area. Thus, in some embodiments of the invention, a plastically deformable or malleable material can be utilized between the heat transfer surfaces.

In some embodiments of the invention, however, a low conductivity material, such as dry air, which typically has a thermal conductivity of about 0.0262 W/m·K (at a temperature of about 300 K and at atmospheric pressure), can be displaced to interrupt the heat path and reduce the heat transfer rate. One skilled in the art will recognize that numerous alternatives to dry air may be used in accordance with the present invention. For example a variety of alternative gasses such as, but not limited to, argon, krypton or xenon may be utilized in practicing the present invention. Additionally a liquid or gel material with an appropriate conductivity may further be substituted for the dry air recited herein. In an alternative embodiment, the low conductivity material may simply be a vacuum. Thus, the body being heated or cooled is decoupled from the heat sink or heat source when the cooling system or heating system is respectively no longer required.

In accordance with one embodiment of the present invention, an actuator is in communication with the thermal bodies. The actuator is disposed such that it can control thermal communication between the bodies. The actuator may be a mechanical actuation means, utilized to facilitate the contacting and/or separating of the thermal bodies. For example, an actuator may be used to effect or promote contacting the heat sink and/or heat source to a chromatographic column. The actuator may utilize, but is not limited to, an electromechanically energized component, such as an electric motor, and/or be pneumatically, or hydraulically motivated. In accordance with one embodiment of the present invention, the invention can be practiced utilizing any of an electromagnetic actuator, a metal actuator, a magnetostrictive device, and/or piezoelectric device. Any of such actuators can be used in combination with one or more lever, screw or other devices that can provide mechanical advantage in facilitating or effecting better contact pressure between the surfaces. In accordance with an alternate embodiment of the present invention, the actuator for contacting and/or separating the bodies undergoing heat transfer may be the thermally conductive material. For example, a shape memory metal, such as a Nitinol metal, may be utilized in establishing and interrupting thermal transfer between bodies.

As illustrated in the embodiment presented in FIGS. 1A and 1B, the invention can comprise a chromatographic column 112 secured or disposed on a first thermal body or mandrel 114 and a heater 126 preferably also helically wrapped around the first thermal body mandrel 114. FIG. 1A and FIG. 1B show an actuator N1, a temperature sensor N2, and a controller N3. First thermal body 114 can comprise or be formed from a high thermal conductivity material such as a metal, a metal alloy, or a composite, and can have a low thermal mass which facilitates rapid heating and cooling of the column 112. In the position shown in FIG. 1A, frustoconically-shaped first thermal body 114 along with column 112 wrapped thereon is disposed distally from a second thermal body 138. Second thermal body 138 comprises a complementarily-shaped feature wherein first thermal body 114 with column 112 can be disposed as discussed below. During heating or temperature ramping processes, first thermal body 114 is disposed as illustrated in FIG. 1A so that the assembly comprising column 112 has a first effective thermal mass heated by heater 126.

In further embodiments of the invention, the first body including first thermal body mandrel 114 and column 112 is disposed to in thermal communication with mating piece second thermal body 138 as illustrated in FIG. 1B. Preferred configurations of the invention involve embodiments wherein mating piece second thermal body 138 effectively serves as a second thermal body. Indeed, in some cases, second thermal body 138 can serve as a heat sink or cold reservoir that facilitates transfers of heat energy from the first body comprising first thermal body 114 and column 112. Some relevant embodiments of the invention involve cold reservoir structures that have a large thermal mass, when compared to the effective thermal mass of the first assembly. In typical operation, the first assembly is disposed in thermal communication with second thermal body 138 during non-heating operations. For example, subsequent to temperature ramping of column 112, the temperature of the column is reduced for the next analytical cycle. This cooling operation can be accelerated by withdrawing heat from the first assembly by way of a heat sink embodied as second thermal mass body 138.

Figures 1C, 1D:
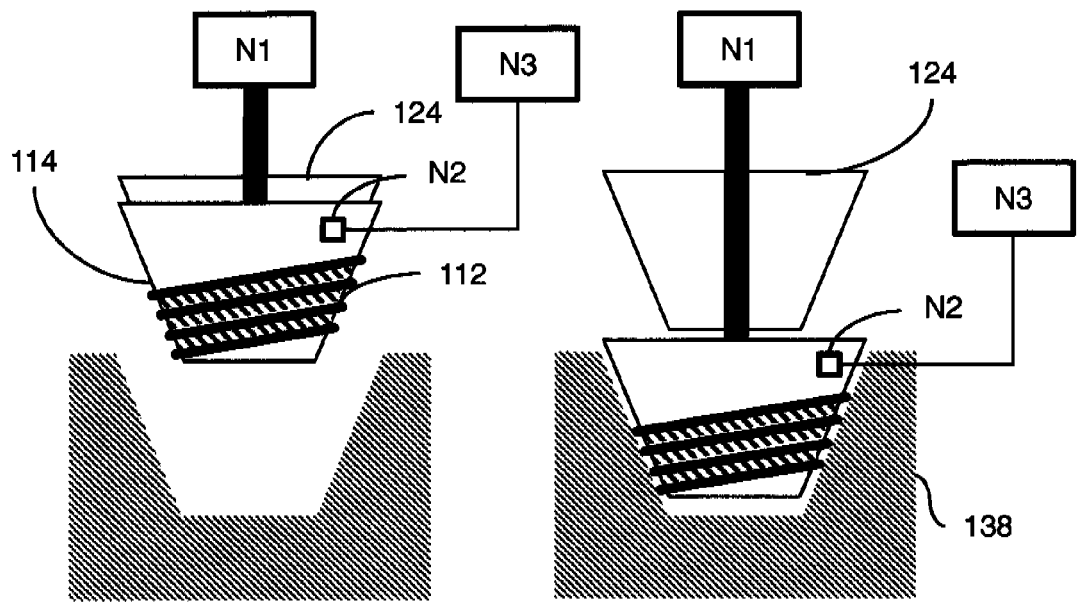

FIGS. 1C and 1D illustrate further embodiments of the invention wherein, as in the above-described embodiments, the first assembly or first body can comprise a first thermal body 114 having at least one chromatographic column 112 in thermal communication therewith. FIG. 1C and FIG. 1D show an actuator N1, a temperature sensor N2, and a controller N3. The first body, in a first configuration illustrated in FIG. 1C, can be in further communication with a second thermal body 124 which can be for example, a heat source having a high thermal mass and, for example, a correspondingly complementarily-shaped features. This configuration can further facilitate heating of the column by reducing the heating load on the heater and/or providing heat regulatory capabilities. In corresponding non-heating operations, the first body can be thermally decoupled from heat source 124 and be coupled in thermal communication with second thermal body 138 at, for example, a complementarily-shaped feature thereof as illustrated in FIG. 1D.

Figure 2A:
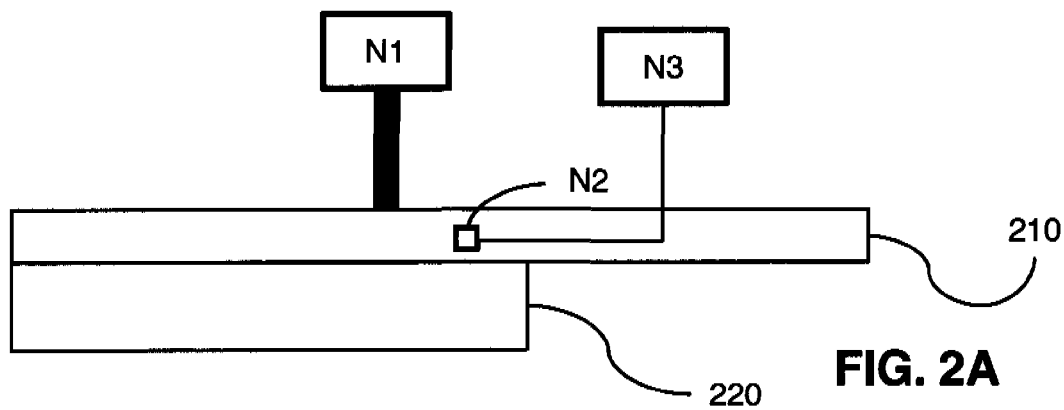
FIGS. 2A and 2B illustrate cooling and heating assemblies in accordance with further embodiments of the invention.
Figure 2B:
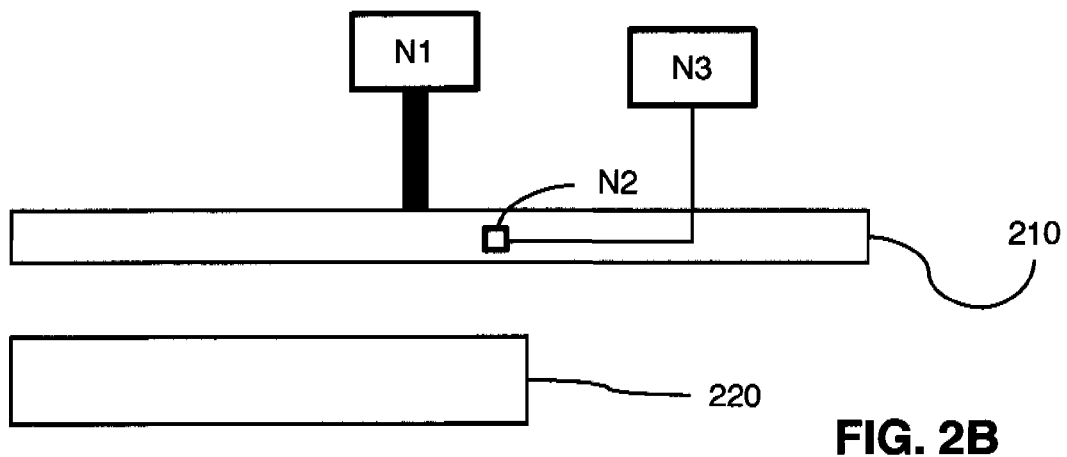
Figure 3A:
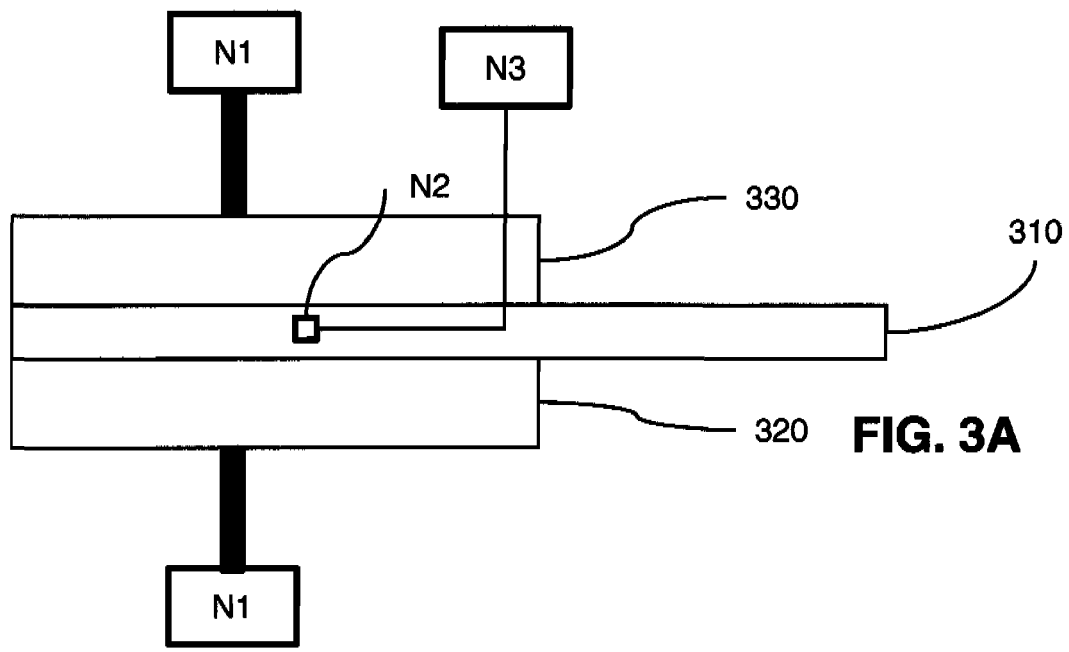
FIGS. 3A and 3B illustrate cooling and heating assemblies in accordance with still further embodiments of the invention.
Figure 3B:
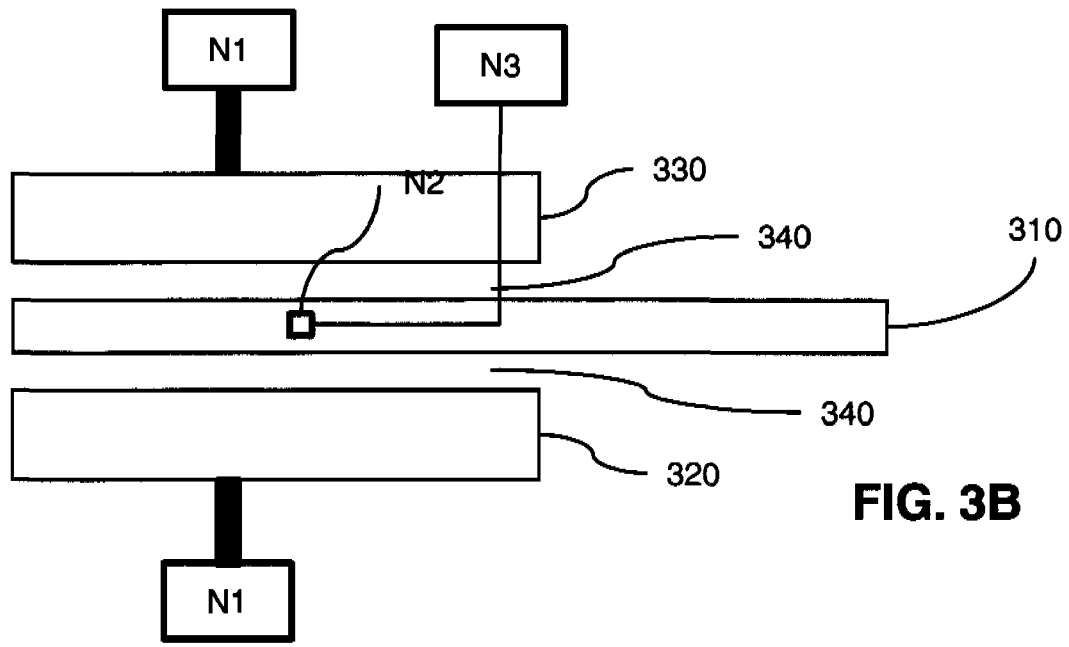

In further embodiments of the invention, one or more chromatographic columns can be mounted in a planar configuration by attaching the column to a plate or using a MEMS column, which is typically manufactured using lithographic techniques. As illustrated in FIG. 2A, one or more cold reservoirs 220 can be pressed against the column 210 so as to provide a heat sink or heat absorbing body and facilitate cooling of column 210. Further still, FIG. 2A to FIG. 2B show an actuator N1, a temperature sensor N2, and a controller N3. In the alternative embodiment illustrated in FIG. 3A, the column 310 can be pressed between two parts of cold reservoirs 320 and 330 to accelerate cooling operations. It is noted that FIG. 3A and FIG. 3B show an actuator N1, a temperature sensor N2, and a controller N3. During non-cooling operations, the column can be thermally insulated from the one or more heat sinks by, for example, introducing an insulation therebetween or by thermally decoupling the column from the heat sinks as shown in FIGS. 2B and 3B. Further embodiments of the invention contemplate utilizing cooling assemblies as a component of cold reservoirs 220, 320, and/or 330.

For example, cooling can be at least partially effected by thermoelectric systems and techniques such as Peltier devices.

Actuation of the first body, the second body or both to affect thermal coupling and/or decoupling can be effected by conventional assemblies and techniques. For example, magnetostrictive devices can be used as components of heat switches that create the heat conductive pathway. Alternatively, actuation of the first body, the second body or both to affect thermal coupling may additionally be effected using a shape memory alloy. Other assemblies such as, but not limited to motorized actuators driven by, for example, electric motors or pneumatic or hydraulic actuators may be utilized.

Figure 4:
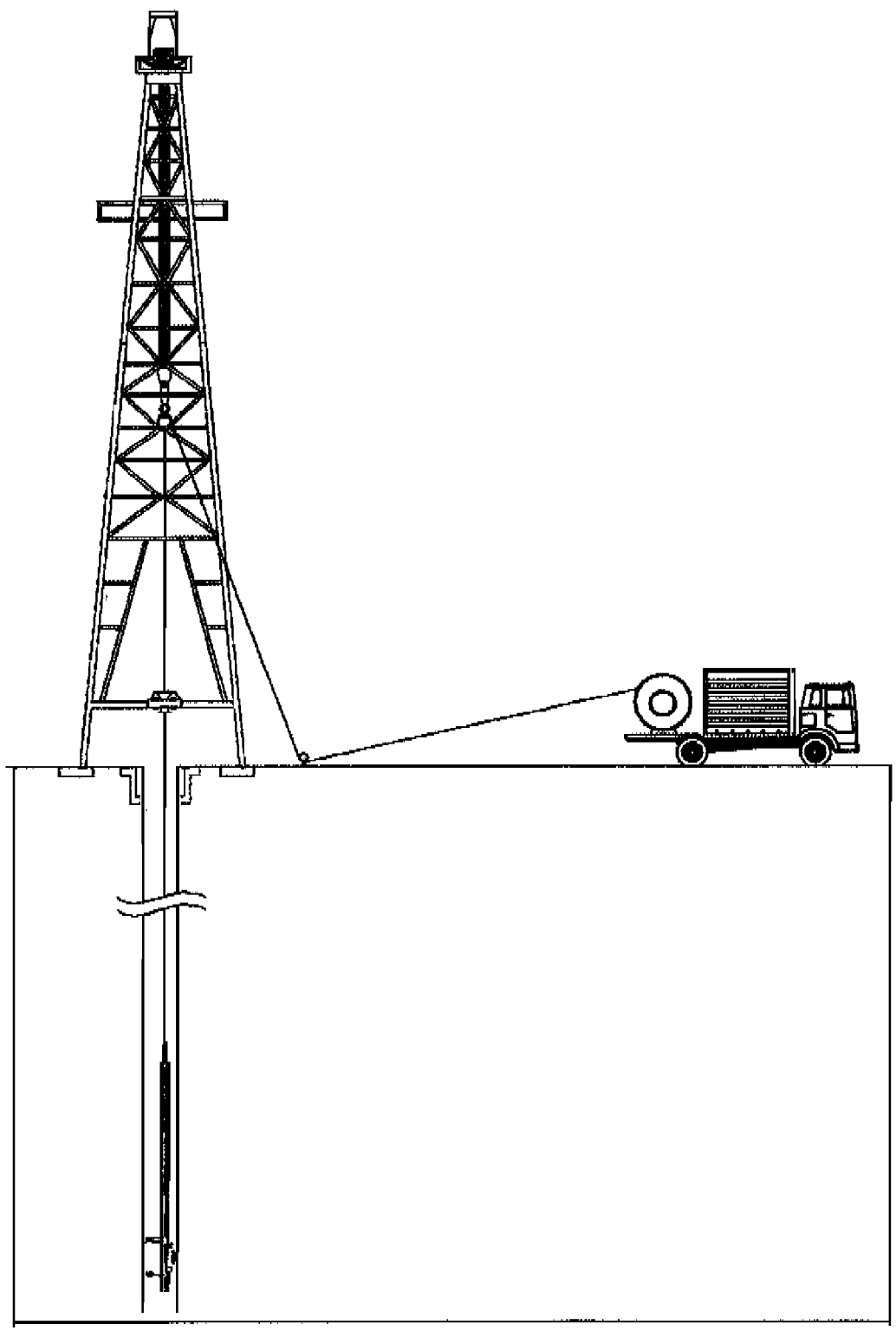
FIG. 4 illustrates a downhole environment in accordance with still further embodiments of the invention.

Having now described some illustrative embodiments of the invention, it should be apparent to those skilled in the art that the foregoing is merely illustrative and not limiting, having been presented by way of example for the purposes of clarity. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. For example, the systems and techniques of the invention can be implemented to heat and/or cool components other than chromatographic columns in a variety of environments including but not limited to downhole environments DH, see FIG. 4.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A system for temperature control of at least one chromatographic column comprising:
    a plurality of thermal bodies comprising one of a heat source, a heat sink or both;
    including a first thermal body and a second thermal body from the plurality of thermal bodies, wherein the first thermal body includes the at least one chromatographic column and one of a inner mating surface, a outer mating surface or both;
    a complementary mating surface of the second thermal body comprises a shape matched in complementary shape and position to the one of the inner mating surface, the outer mating surface or both of the first thermal body whereby the second thermal body is in thermal communication with the first thermal body; and
    an actuator configured to facilitate movement during operation so as to control thermal communication between one of at least a portion of the first thermal body and at least a portion of the second thermal body.

2. The system of claim 1, further comprising a heater in thermal communication with the first thermal body.

3. The system of claim 1, wherein the actuator is a mechanical actuator.

4. The system of claim 1, further comprising a temperature sensor disposed so as to measure a temperature of the at least one chromatographic column and to generate a signal that is representative of the measured at least one chromatographic column temperature.

5. The system of claim 4, further comprising a controller configured to receive the signal from the temperature sensor, and to generate an actuation signal to the actuator based at least partially on the measured at least one chromatographic column temperature.

6. The system of claim 1, wherein the first thermal body is a heat source and the second thermal body is a heat sink.

7. The system of claim 1, wherein the at least one chromatographic column is disposed in a downhole environment.

8. The system of claim 1, wherein at least one thermal body of the plurality of thermal bodies consists of one of at least one liquid, at least one solid, a non-atmospheric gas consisting of argon, krypton and xenon or some combination thereof.

9. The system of claim 1, wherein at least one thermal body of the plurality of thermal bodies consist of one of at least one liquid, a gel material, at least one solid or a non-atmospheric gas consisting of argon, krypton and xenon.

10. The system of claim 1, wherein the first thermal body and second thermal body have complementarily-shaped features respectively to one another.

11. A method of characterizing an analyte in a chromatographic system, the chromatographic system includes a plurality of thermal bodies comprising one of a heat source, a heat sink or both, the chromatographic system comprising:
    introducing the analyte into the chromatographic column, the chromatographic column having a first thermal body and a second thermal body from the plurality of thermal bodies associated therein, wherein the first thermal body has one of a inner mating surface, a outer mating surface or both;
    a complementary mating surface of the second thermal body comprises a shape matched in complementary shape and position to the one of the inner mating surface, the outer mating surface or both of the first thermal body whereby the second thermal body is in thermal communication with the first thermal body;
raising the temperature of the chromatographic column from a first temperature to a second temperature; and
thermally coupling the first thermal body to the second thermal body, wherein a facilitating means provides movement of one of the first thermal body or the second thermal body during operation.

12. The method of claim 11, further comprising thermally decoupling the chromatographic column from a heat sink.

13. The method of claim 11, further comprising disposing the system in a downhole environment.

14. The method of claim 11, wherein thermally coupling the first thermal body to the second thermal body comprises contacting at least a portion of the first thermal body against at least a portion of the second thermal body.

15. The method of claim 11, wherein raising the temperature of the chromatographic column comprises thermally coupling at least a portion of the first thermal body to a heated body.

16. The method of claim 11, further comprising measuring the temperature of the first thermal body.

17. The method of claim 16, further comprising thermally decoupling the chromatographic column from a heat sink when the measured temperature of the first thermal body is less than or equal to a threshold temperature.

18. The method of claim 17, further comprising introducing another analyte into the chromatographic column.

19. The method of claim 18, further comprising:
raising the temperature of the first thermal body; and
thermally coupling at least of portion of the second thermal body to at least a portion of the first thermal body after raising the temperature of the first thermal body.

20. The method of claim 11, wherein the first thermal body has a lower thermal mass as compared to the second thermal body.

21. The method of claim 11, wherein the thermal coupling is a conductive thermal coupling.

22. The method of claim 11, wherein the first thermal body is a heat source and the second thermal body is a heat sink.

23. The method of claim 11, wherein the facilitating means is at least one actuator.

24. At least one temperature controlled chromatographic column disposed in a downhole environment comprising:
a plurality of thermal bodies comprising one of a heat source, a heat sink or both;
a first thermal body and a second thermal body from the plurality of thermal bodies, wherein the first thermal body includes the at least one temperature controlled chromatographic column and one of a inner mating surface, a outer mating surface or both;
a complementary mating surface of the second thermal body comprises a shape matched in complementary shape and position to the one of the inner mating surface, the outer mating surface or both of the first thermal body whereby the second thermal body is in thermal communication with the first thermal body; and
an actuator configured to facilitate movement during operation so as to control thermal communication between one of at least a portion of the first thermal body and at least a portion of the second thermal body.

25. The at least one temperature controlled chromatographic column of claim 24, further comprising a thermally conductive material disposed on at least one portion of the surface of the second thermal body.

26. The at least one temperature controlled chromatographic column of claim 25, wherein the thermally conductive material comprises a non-oxide forming material.

27. The at least one temperature controlled chromatographic column of claim 24, further comprising a heater in thermal communication with the first thermal body.

28. The at least one temperature controlled chromatographic column of claim 24, wherein the actuator is a mechanical actuator.

29. The at least one temperature controlled chromatographic column of claim 24, further comprising at least one temperature sensor disposed so as to measure a temperature of the chromatographic column and to generate a signal that is representative of the measured chromatographic column temperature.

30. The at least one temperature controlled chromatographic column of claim 29, further comprising a controller configured to receive the signal from the at least one temperature sensor, and to generate an actuation signal to the actuator based at least partially on the measured chromatographic column temperature.

31. The at least one temperature controlled chromatographic column of claim 24, wherein the first thermal body is a heat source and the second thermal body is a heat sink.

32. At least one temperature controlled chromatographic column comprising:
a plurality of thermal bodies comprising one of a heat source, a heat sink or both;
a first thermal body and a second thermal body from the plurality of thermal bodies, wherein the first thermal body includes the at least one temperature controlled chromatographic column and one of a inner mating surface, a outer mating surface or both;
a complementary mating surface of the second thermal body comprises a shape matched in complementary shape and position to the one of the inner mating surface, the outer mating surface or both of the first thermal body whereby the second thermal body is in thermal communication with the first thermal body;
another thermal body from the plurality of thermal bodies includes a heat source; and
an actuator configured to facilitate movement during operation so as to control thermal communication between one of at least a portion of the another thermal body and at least a portion of the second thermal body.

33. A system for temperature control of at least one chromatographic column comprising:
a plurality of thermal bodies comprising one of a heat source, a heat sink or both;
including a first thermal body from the plurality of thermal bodies, wherein the first thermal body includes the at least one chromatographic column;
a second thermal body from the plurality of thermal bodies having a surface such that a thermally conductive material is disposed on at least one portion of the surface whereby the thermally conductive material comprises a non-oxide forming material; and
an actuator configured to facilitate movement during operation so as to control thermal communication between one of at least a portion of the first thermal body and at least a portion of the second thermal body.

* * * * *